United States Patent [19]

Cabrera et al.

[11] Patent Number: 4,580,558

[45] Date of Patent: Apr. 8, 1986

[54] LASER INSTRUMENT

[75] Inventors: Rene J. Cabrera, Stoughton; Thomas W. Eagar, Belmont, both of Mass.

[73] Assignee: Codman & Shurtleff, Inc., Randolph, Mass.

[21] Appl. No.: 594,168

[22] Filed: Mar. 28, 1984

[51] Int. Cl.⁴ .............................................. A61B 17/36
[52] U.S. Cl. .............................. 128/303.1; 219/121 L; 128/303 R
[58] Field of Search .................. 219/121 LC, 121 LJ, 219/121 LP, 121 LR, 121 LT, 121 L; 128/305, 303.1, 395-398, 303 R

[56] References Cited

U.S. PATENT DOCUMENTS

| 4,388,517 | 6/1983 | Schulte et al. | 219/121 LJ |
| 4,436,979 | 3/1984 | Nilsen | 219/121 LC |

FOREIGN PATENT DOCUMENTS

| 0033958 | 8/1981 | European Pat. Off. | 128/303.1 |
| 2207387 | 8/1973 | Fed. Rep. of Germany | 128/303.1 |
| 58-73366 | 5/1983 | Japan . | |
| 8203305 | 9/1982 | World Intel. Prop. O. | 128/303.1 |
| 2060397 | 5/1981 | United Kingdom | 128/303.1 |

Primary Examiner—Kyle L. Howell
Assistant Examiner—Ruth S. Smith
Attorney, Agent, or Firm—Donal B. Tobin

[57] ABSTRACT

A surgical tool for intercepting laser energy after it has energized a target site but before it energizes adjacent tissue. The instrument includes substrate of material having a high thermal conductivity for transmitting laser energy away from the surgical site and a highly absorbent surface material for absorbing radiant energy at the wavelength of the incident laser.

14 Claims, 8 Drawing Figures

LASER INSTRUMENT

FIELD OF THE INVENTION

The present invention relates a tool useful in a laser environment, to absorb rather than reflect laser energy, and more particularly to a surgical instrument used with a surgical laser to absorb laser energy after it has energized tissue at a desired surgical site, but before it energizes adjacent tissue.

BACKGROUND OF THE INVENTION

High energy electromagnetic energy beams such as those produced by lasers have been found to be very useful in performing a variety of medical procedures.

The most commonly used surgical lasers are argon lasers, neodymium in yttrium aluminum garnet (Nd-YAG) and carbon dioxide ($CO_2$) lasers. Helium, neon and ruby lasers have also been used to a lesser extent as surgical lasers. Each of these lasers generates light of different wavelengths, which in turn, interacts differently with different types of tissues. For example, an argon laser is absorbed well by pigmented tissue and is primarily used in ophthamology to coagulate tissue. One principal use is to fuse the retina back into place. An Nd-YAG laser penetrates more deeply than an argon laser and is principally used as a coagulator. It has been used effectively for gastroenterology for coagulating ulcers and lesions. The Nd-YAG works well for gastroenterology because its beam can be carried by a fiber deep inside the body to places which are relatively inaccessible by conventional surgical means.

The $CO_2$ laser is essentially a surface device and does not penetrate very deeply into tissue. It is most effectively used as a cutter, because it can cut quickly through tissue layer by layer by applying large amounts of heat directly on the surface to vaporize the tissue. Very high power levels can be delivered by a $CO_2$ laser and it can even be used to vaporize bone. $CO_2$ lasers have been particulary effective in gynecology surgery, where they can be used to split open a fallopian tube or to remove adhesions from organs such as ovaries or fallopian tubes. Particularly in the gynecological environment, it is important to prevent the $CO_2$ laser beam from traveling farther into the tissue than is necessary. In fallopian tube surgery, it is desirable to split the anterior surface of the fallopian tube without damaging the posterior surface. It would be very useful to have an instrument which could be inserted into the fallopian tube so that only one surface of the tube would be affected by the $CO_2$ laser beam.

$CO_2$ lasers are very good for removing adhesions which adhere to various organs. Sometimes adhesions will surround the fallopian tubes and the ovaries. If the ovary is otherwise in good condition, one would wish to shield the ovary and the surrounding organs and tissue from the $CO_2$ beam while the adhesion is vaporized with the $CO_2$ laser. Adhesions are usually made of connective tissue which can extend enormously around the adhesion site. One wishes to destroy the adhesion without damaging the surrounding vital organs.

Because of the uses to which an argon surgical laser is put, it is not often necessary to insert laser beam absorption tools into the surgical site. However, it is desirable to assure that surgical instruments used in the operating room environment will not reflect the laser beam so that it would be useful to have laser-absorbing coatings on the apparatus used in the vicinity of an argon laser.

Similarly, because of the uses to which an Nd-YAG surgical laser is put, specific laser beam absorbing tools are not generally used for the YAG laser. However, again, it is also useful to render surgical tools used in the vicinity of the surgical site laser beam absorbing rather than reflecting.

With $CO_2$ surgical lasers, it is particularly useful to have instruments which are specifically designed to act as backstops and shields for laser beams to intercept the laser beam after it has been delivered to the surgical site and before it can energize surrounding tissue, organs or bone. It is also useful to render all of the surgical instruments that are used in the vicinity of the $CO_2$ laser absorbing so that they will not reflect the $CO_2$ beam onto healthy organs, tissue and bone.

In the past, attempts have been made to provide surgical tools which would absorb laser energy by, for example, changing the color of the surgical tool from its shiny, silvery stainless steel appearance to a dull black finish. Although this may be effective in some circumstances, physicians have found the problem of absorbing undesired laser beams significant enough to cause many physicians to limit their use of laser surgical apparatus because of the problems in properly controlling the path of the laser beam in and around the surgical site.

A laser beam has sufficient energy to heat a tool up to such high levels that it is hot to the touch, and thus is difficult for the surgical personnel to handle and could also burn the patient. Laser surgical pulses are, in some instances, powerful enough to cause metal instruments, for example stainless steel instruments, to glow and sometimes to deteriorate under the effect of the laser beam. This is quite clearly an undesired result, which would obviously discourage the surgeons from using laser surgical tools. If a surgical tool could be provided which would effectively absorb laser energy beams so that they would not impinge upon tissue outside the desired surgical site, one expects that the use of laser surgical tools would increase and that laser surgery could be more reliable.

SUMMARY OF THE INVENTION

The present invention provides a tool which is a highly efficient laser beam absorber but which, under normal operating conditions, will dissipate the heat rapidly and thus will not heat up appreciably so that the material from which the tool is made will not deteriorate, glow or become too hot to be handled by the surgical personnel. The present invention can also be used as a coating for operating tools and hardware so that they will absorb and not reflect an incident beam of laser energy.

This invention can be incorporated into a tool which provides a backstop intercepting laser energy after it has energized a target site but before it energizes adjacent tissue, organs or bone in the vicinity of the surgical site. The instrument includes a substrate of material which has a high thermal conductivity for transmitting received laser energy away from the surgical site so that the instrument does not increase appreciably in temperature. A surface material is applied to the entirety of the peripheral surface of the substrate. The surface material has a high absorptivity for radiant energy at the wavelength of the laser whose energy it is intended to intercept. The surface material has a thickness which is high enough to provide high absorptivity but thin enough to permit absorbed energy to be conducted to the high conductivity substrate. In the preferred embodiment, the thickness of the surface material is at least twenty-five percent (25%) of the wavelength of the impinging laser energy but not greater than 0.001 inch (25 microns). The most preferred embodiment of the present invention uses a substrate material of aluminum with a coating of anodized aluminum oxide. Other combinations of highly absorbent surface material and highly conductive substrate material can be used, for example stainless steel over copper or even ceramic material over copper, aluminum, gold or some other highly conductive material.

In order to further facilitate cooling of the instrument, channels can be introduced into the substrate material to provide a means for delivering irrigation fluid, usually a saline solution, through the channel to cool the instrument and to provide irrigation at the surgical site. The instrument may be made in a flat embodiment similar to the shape of a tongue depressor with channels running generally axially from the proximal end of the instrument to the distal end. The proximal end of the instrument is connected to a handle which can provide fluid communication to a source of irrigation fluid.

In another embodiment, the instrument can be a rod with a highly conductive core and a highly absorbent surface. This rod is particularly useful in fallopian tube surgery. This rod could also have an annular channel through its center for the passage of cooling fluid.

The present invention can also be used to render the surface of a wide variety of conventional surgical instruments laser beam absorbing so that laser pulses will not inadvertently bounce off surgical instruments or surrounding surgical apparatus. If the surgical instrument were made of a highly conductive material, the highly absorbent surface material could be merely placed on the instrument. If on the other hand the instrument had a low thermal conductivity, a cladding of high thermal conductivity material like copper or aluminum could be placed over the critical parts of the surgical instrument and that cladding material could be coated with a highly absorbent surface material.

This invention also has application in fields other than medicine. Lasers are used in a variety of manufacturing environments and the tools and apparatus that are used with the laser should also have a non reflective surface to protect the instruments themselves and to protect the personnel that operate the machinery.

These and other features and advantages of the present invention will become apparent from the following detailed description of the preferred embodiment taken in conjunction with the following drawings.

DETAILED DESCRIPTION OF THE PREFERRED EMBODIMENT

Figure 1:
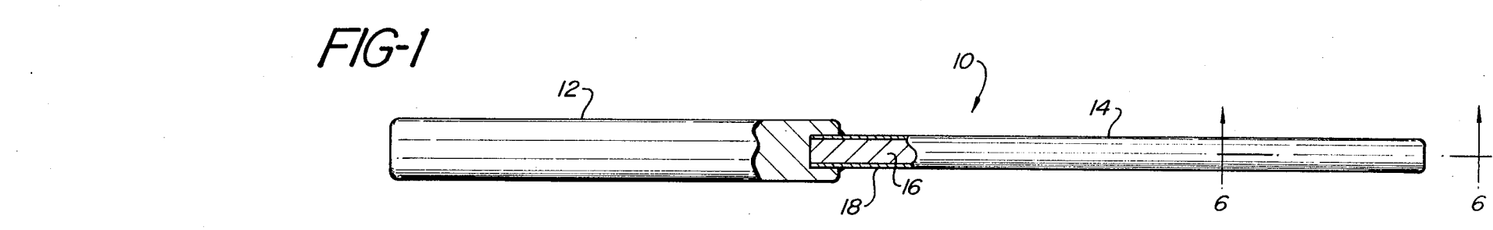
FIG. 1 shows a plan view, partly in section, of a particular embodiment of the present invention.

Referring now to FIG. 1 there is shown instrument 10 with handle 12 and rod 14 made of solid, high thermal conductivity substrate 16 and high absorptivity coating 18. In the preferred embodiment, the core is made of aluminum 6061-T6 with a satin finish prepared in the manner described later in this application, and the coating 18 is made of anodized aluminum oxide. Aluminum 6061-T6 was preferred because it has a high corrosion resistance so it is very satisfactory for medical instruments which are used in a saline solution environment. This aluminum is also readily available and has a high thermal conductivity.

The aluminum/aluminum oxide embodiment of FIG. 1 is particularly preferred for use with a carbon dioxide laser. It has been found that the thickness of coating 18 should be a significant fraction of the wavelength of the incident laser light. We have found that 40% is satisfactory with a $CO_2$ laser light having a wavelength of about 10.6 microns. A 4 micron thickness worked well as a minimum thickness for coating 18 in the present invention. The minimum thickness is also controlled to some extent by the limitations of the anodizing process where a two (2) micron minimum thickness prevails. Thicknesses as high as 12 microns were tried and worked satisfactorily. The maximum thickness can be defined qualitatively as that thickness where the coating 18 starts to act as a thermal insulator and inhibits the heat from being readily conducted to the high thermal conductivity substrate material. One does not wish to have a high thermal build-up in coating layer 18, which would tend to increase the temperature of the coating and perhaps increase the likelihood that the surface could deteriorate or that the instrument could become hot to the touch.

For incident electromagnetic energy of wavelengths different from that of a $CO_2$ laser (10.6 microns) different thicknesses of surface material 18 could be used. For example, with an Nd-YAG laser whose wave length is about 1 micron or 10% of a $CO_2$ laser, the thickness of coating 18 could be much thinner. With an Nd-YAG laser, one might consider different deposition techniques other than anodizing. It is believed that the anodizing coating has a minimum satisfactory thickness, which is a function of the anodizing process. Other deposition techniques, like sputtering or other techniques well-known in the electronics industry where very thin layers of material are placed on base material, could be used. For certain wavelengths, ceramic coatings could be placed on high thermal conductivity substrates.

For the $CO_2$ wavelength, instead of using aluminum oxide over aluminum, one could substitute stainless steel over copper or a variety of other combinations of a highly absorbent coating over a highly conductive substrate material.

The production of high absorptivity surface material requires a reduction in the number of free electrons. Reflectivity, or the inverse of absorptivity, is proportional to the number of free electrons in the material.

Thus, something which is a good reflector is also usually a good thermal conductor, since most of the heat is conducted by free electrons, and it is also usually a good electrical conductor, since electricity is conducted by free electrons. On the other hand, a good absorber is usually a good thermal insulator and a poor electrical conductor. Thus, any material which has a relatively high electrical resistance and a low thermal conductivity would be a good absorber because it has few free electrons and would be a good surface material for use with the present invention. In the present invention, a composite material has been designed which has both high absorptivity of laser light on the surface and high thermal conductivity in the bulk. Such a combination of properties is not possible in a monolithic material.

Figure 2:
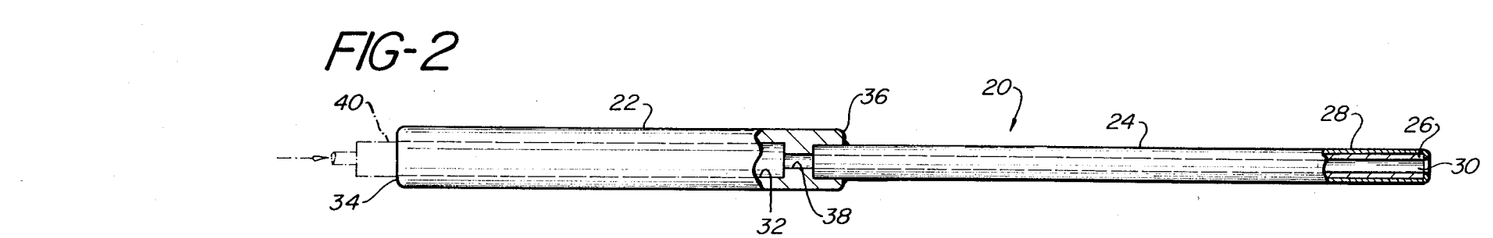
FIG. 2 shows a plan view, partly in section, of a second embodiment of the invention.

Referring now to FIG. 2 there is shown a modification of the embodiment of the instrument of FIG. 1 which includes an instrument 20 adapted for use with a cooling fluid. Instrument 20 has a handle 22 and a rod 24. Rod 24 has a substrate 26 and a coating 28. However, substrate 26 is annular in shape and has an opening 30 extending throughout its entire length. Handle 22 includes an opening 32 extending from its proximal end 34 axially along almost the entirety of handle 22. Near the distal end 36 of handle 22, opening 32 changes to a reduced diameter portion 38, which diameter is essentially the same diameter as that of opening 30 in rod 24. Shown in phantom in FIG. 2 is an appropriate connection 40 for connecting handle 22 to a source of cooling fluid. The cooling fluid may be a conventional saline solution that is used commonly during surgical procedures. This solution carries away the heat which has been dissipated by the bulk metal of the instrument.

Figure 3:
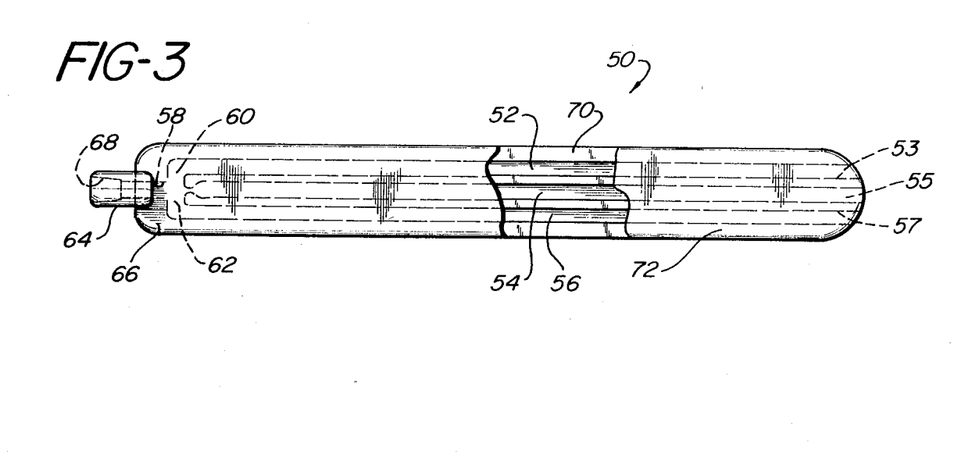
FIG. 3 shows a plan view, partly in section, of a third embodiment of the present invention.
Figure 4:
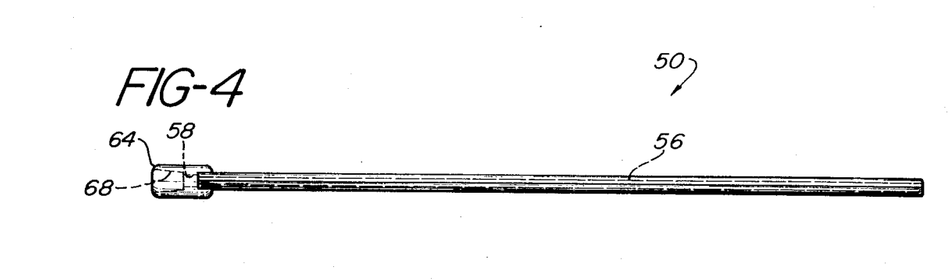
FIG. 4 shows a side view of the embodiment of FIG. 3.
Figure 5:
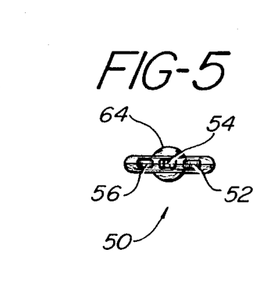
FIG. 5 shows an end view of the embodiment of FIG. 3.
Figure 6:
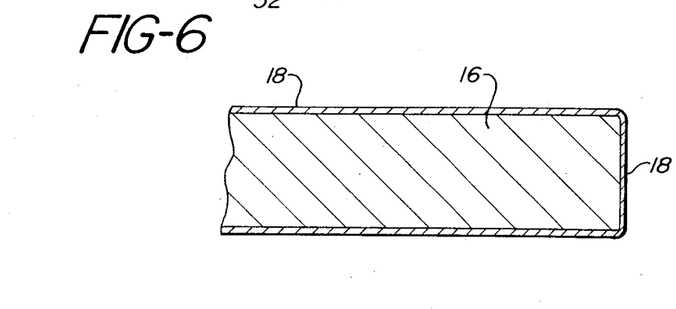
FIG. 6 shows an enlarged cross-section taken along lines 6—6 of FIG. 1.

Referring now to FIGS. 3, 4 and 5, there is shown another modification of the invention shown in FIG. 1. Instrument 50 shown in FIG. 3 is shaped generally like a tongue depressor and has an axial dimension much greater than its transverse dimension. Instrument 50 has three channels 52, 54 and 56 extending from a single opening 58 at the proximal end of instrument 50 to three openings 53, 55 and 57 at the distal end of instrument 50. Branches 60 and 62 extend from opening 58 to channels 52 and 56. Handle portion 64 is firmly affixed to the proximal portion 66 of instrument 50 and includes an opening 68 extending completely therethrough to provide fluid communication with opening 58 in the proximal end of instrument 50 to provide a fluid communication from a source of irrigation fluid (not shown) to the instrument 50. Instrument 50 is constructed similarly to instrument 10 shown in FIG. 1 and includes a substrate material 70 covered by a coating 72. Substrate 70 has a high thermal conductivity, and coating 72 has a high absorptivity.

Figures 7, 8:
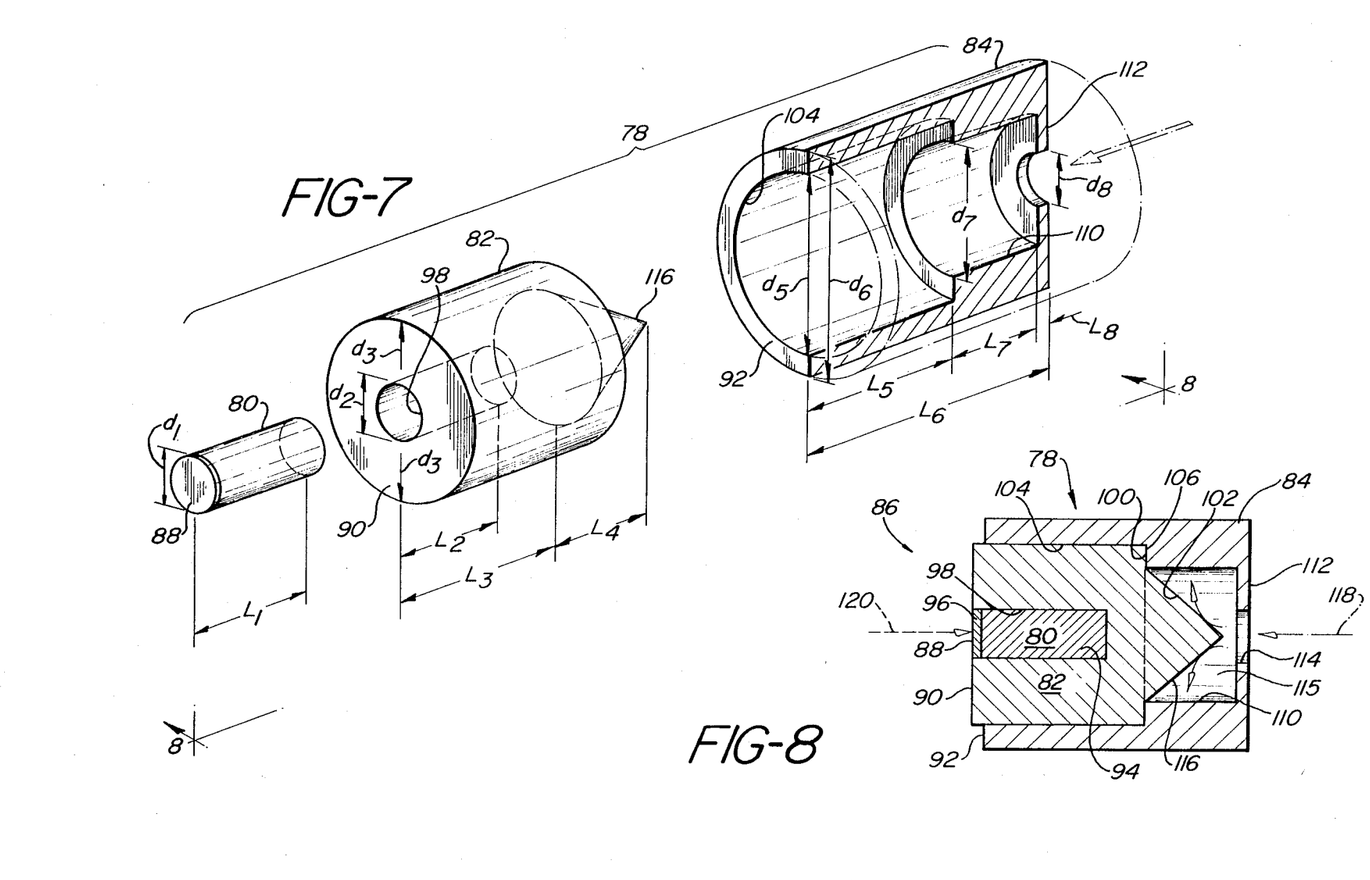
FIG. 7 shows an exploded perspective, partly in section, of a test fixture used in measuring surface properties of the present invention.
FIG. 8 shows an assembled cross-sectional view of the test fixture of FIG. 7 taken along lines 8—8 in FIG. 7.

Referring now to FIGS. 7 and 8, there is shown a test fixture 78 used to determine the absorptivity of various test specimens. FIG. 7 shows an exploded perspective view of the three parts of the fixture, including a test specimen 80, a holder 82 into which test specimen 80 is inserted and a housing 84 into which holder 82 and test specimen 80 are inserted together. As shown better in FIG. 8, of fixture 78, surface 88 of test specimen 80, and surface 90 of holder 82 are aligned flush with one another and protruding slightly beyond surface 92 of housing 84.

Test specimen 80 is made of a composite material which has a solid aluminum substrate 94 having a high thermal conductivity and a coating 96 which has a high absorptivity. Holder 82 has a bore 98 into which test specimen 80 is press fitted. Bore 98 extends into holder 82 a sufficient distance to permit exterior surface of test specimen 80 to be flush with the exterior surface 90 of holder 82. The other end of holder 82 from surface 90 includes a circumferential flange 100 and a cone 102 which extends in a direction away from surface 90 of holder 82.

Housing 84 includes a bore 104 into which holder 82 slides with a clearance fit. Bore 104 extends a sufficient distance into housing 84 so that the exterior surface 90 of holder 82 is protruding slightly beyond exterior surface 92 of housing 84. Holder 84 has a flange 106 which mates with flange 100 of holder 82 and acts as a stop against which holder 82 bottoms when it is slid into housing 84. Housing 84 has a second bore 110 extending from flange 106 in a direction away from surface 92. The diameter of bore 110 is approximately equal to the diameter of the base of cone 102 of holder 82. Bore 110 ends in a wall 112 which has a bore 114 in it through which a laser beam may be directed at the cone surface 116 of cone 102 so that all of the laser energy will be completely trapped and absorbed by holder 82 and housing 84. Housing 84 is used principally to provide a cavity 115 about cone surface 116 to trap laser energy directed at holder 82 along line 118.

The dimensions of fixture 78 are listed in Table I below:

TABLE I

| Diameter (in inches) | | Length (in inches) | |
| --- | --- | --- | --- |
| D-1 | .093 | L-1 | .125 |
| D-2 | .093 | L-2 | .125 |
| D-3 | .280 | L-3 | .220 |
| D-5 | .281 | L-4 | .124 |
| D-6 | .380 | L-5 | .172 |
| D-7 | .187 | L-6 | .380 |
| D-8 | .093 | L-7 | .156 |
| | | L-8 | .052 |

Test fixture 78 is used as follows. Test fixture 78 is mounted in fixed orientation and is maintained at a known ambient temperature. A laser beam designated schematically as 118 is directed through opening 114 into cavity 115 against surface 116 of cone 102. The entirety of the laser energy is contained in cavity 115 and absorbed into holder 82 and housing 84 which are in intimate thermal contact. The mass of holder 82 is large so that all of the energy will be easily absorbed so as to elevate the temperature of holder 82 and housing 84. The temperature of housing 84 can be measured by conventional means, for example using a thermistor (not shown) attached to housing 84 and connected to suitable temperature reading instrumentation (also not shown).

After the temperature change in housing 84 has been noted for a particular pulse duration and power level, holder 82 and test specimen 80 and housing 84 are permitted to return to a known ambient temperature. The laser beam is then directed along line 120 toward surface 88 of coating 96 on test specimen 80, and the temperature of housing 84 is again measured. This time, since some of the energy directed along line 120 at test specimen 80 will be reflected and not absorbed by the housing the temperature rise will be smaller. The ratio of the change of temperature of housing 84 caused by the laser beam directed along line 120 ($\Delta T_2$) divided by the change of temperature caused by the laser beam directed along line 118 ($\Delta T_1$) is defined as the absorptivity of the surface of the test specimen 80.

In attempting to make the laser instrument of the present invention, several approaches were tried. Since most surgical instruments are made of stainless steel or titanium, a number of test rods were made of these materials with different surface finishes. This approach followed the teaching of the prior art that a suitable laser tool should be achievable by proper surface treatment. Two specimens each were made with stainless steel, stainless steel with a bright surface finish, stainless steel with a glass bead surface finish, stainless steel with a satin finish and stainless steel with a black oxide finish. Also, two test specimens each were made of titanium with a bright surface finish, a glass bead surface finish, a satin surface finish and a blue anodized surface finish. One specimen of each set was subjected to a $CO_2$ laser with a ¼ millimeter to ½ millimeter spot size for four seconds at a power level of 50 watts. The other specimen from each set was subjected to the same $CO_2$ laser with the same spot size for the same period of time but at a 20 watt power level.

The results of these tests are shown in the following Table II:

tion at the surface of the test specimen. The relatively poor thermal conductivity of titanium and stainless steel permits rapid heat build up on the surface of the test specimen 80. If the power level is sufficient, the metal is vaporized and oxidizes in the air, thus, generating excess heat. The heat from both oxidation and the laser beam can exceed the total energy of the incident laser beam as measured in the cavity 115.

Another reason for the absorptivity greater than 1 may be that the hole in the cavity may be too large a fraction of the cavity surface area, so that some of the laser energy escapes back out of hole 114 of test fixture 78, however, loss of power through this hole is small because almost all of the samples shown in Table II ignited or oxidized when tested, it is concluded that the samples were subjected to too much power (50 watts and 20 watts) for too long a time (4 seconds).

A second test was conducted in which two sets of specimens were made of the material specified in Table III, particularly stainless steel with a bright finish, glass bead finish, satin finish and black oxide finish. Titanium test samples were prepared with a bright finish, a glass bead finish, a satin finish and a blue anodized finish. In addition, aluminum test samples prepared with a bright

TABLE II

| Material | Finish | $\Delta T_1$ = Resistance Ohms | Power Levels | $\Delta T_2$ | A = Absorptivity $\Delta T_2/\Delta T_1$ | Remarks |
|---|---|---|---|---|---|---|
| 1. Stn. St. | Bright | 14.9 | 50 W | 5.0 | .36 | Short Flash |
| 1. Stn. Stl. | Bright | 7.0 | 20 W | 1.3 | .19 | No Flash |
| 2. Stn. Stl. | Glass Bead | 14.9 | 50 W | 14.8 | .99 | Incandescent |
| 2. Stn. Stl. | Glass Bead | 7.0 | 20 W | 3.3 | .47 | — |
| 3. Stn. Stl. | Satin | 14.9 | 50 W | 15.8 | 1.06 | Incandescent |
| 3. Stn. Stl. | Satin | 7.0 | 20 W | 8.3 | 1.19 | Incandescent |
| 4. Stn. Stl. | Black Oxide | 14.9 | 50 W | 15.2 | 1.02 | Incandescent |
| 4. Stn. Stl. | Black Oxide | 7.0 | 20 W | 8.2 | 1.17 | Incandescent |
| 5. Titanium | Bright | 14.9 | 50 W | 14.6 | .98 | Incand. Spurts of Material Ejected |
| 5. Titanium | Bright | 7.0 | 20 W | 2.0 | .29 | No Flash |
| 6. Titanium | Glass Bead | 14.9 | 50 W | 16.0 | 1.07 | Incandescent |
| 6. Titanium | Glass Bead | 7.0 | 20 W | 4.0 | .57 | Small Spot on Surface |
| 7. Titanium | Satin | 14.9 | 50 W | 19.3 | 1.3 | Incandescent |
| 7. Titanium | Satin | 7.0 | 20 W | 2.8 | .4 | Small Spot |
| 8. Titanium | Blue Anodize | 14.9 | 50 W | 16.3 | 1.09 | Incandescent |
| 9. Titanium | Blue Anodize | 7.0 | 20 W | 2.3 | .33 | Small Spot |

Observations from Table II Tests

All of the surfaces except the bright finished stainless steel glowed brightly with the 50 watt laser exposure. The surfaces number 3 and number 4, that is stainless steel with a satin finish and stainless steel with a black oxide finish also glowed at 20 watts. The incandescent regions of these specimens, as shown in the Remarks column of the table, ejected a certain amount of smoke. Surface number 5, that is bright finish titanium, seemed to eject a fine powder.

The stability of the laser under pulsed mode at 50 watts and 20 watts was checked. At 50 watts the variation in total pulse energy was found to be 1.8% of the mean value over 8 pulses. At 20 watts, the variation in total pulse energy was found to be 4% of the mean value over 10 pulses. Extra variations may be due in part to noise in the detector. These are much more significant at the lower power level.

The table shows that some of the absorptivities are greater than 1, that is the energy absorbed by the test surface was greater than 100% of the energy delivered by the pulse. It is possible that these apparent absorptivities of greater than 1 are due to an exothermic reacfinish, glass bead finish, satin finish and a blue anodized finish were also tested. One of each of the sets of test specimens was subjected to a $CO_2$ laser with a ¼ to ½ millimeter spot size for one second exposures at a power level of 40 watts. The other of the set was exposed to the same $CO_2$ laser with the same spot size for the same period of time but at a 30 watt power level. The results of these tests are shown in Table III.

TABLE III

| Material | Finish | $\Delta T_1$ | $\Delta T_2$ | Power Levels | A-Absorptivity $\Delta T_2/\Delta T_1$ |
|---|---|---|---|---|---|
| 1. Stn. Stl. | Bright | 4.62 ± .3 | 1.0 | 40 W | .22 |
| 1. Stn. Stl. | Bright | 2.91 ± .04 | .6 | 30 W | .21 |
| 2. Stn. Stl. | Glass Bead | 4.62 | 1.4 | 40 W | .30 |
| 2. Stn. Stl. | Glass Bead | 2.91 | 1.0 | 30 W | .34 |
| 3. Stn. Stl. | Satin | 4.62 | 3.35 | 40 W | .73 |
| 3. Stn. Stl. | Satin | 2.91 | 2.625 | 30 W | .90 |
| 4. Stn. Stl. | Black Oxide | 4.62 | 2.3 | 40 W | .50 |
| 4. Stn. Stl. | Black Oxide | 2.91 | .875 | 30 W | .30 |
| 5. Titanium | Bright | 4.62 | 1.15 | 40 W | .25 |
| 5. Titanium | Bright | 2.91 | .75 | 30 W | .26 |

TABLE III-continued

| Material | Finish | $\Delta T_1$ | $\Delta T_2$ | Power Levels | Absorptivity $\Delta T_2/\Delta T_1$ |
|---|---|---|---|---|---|
| 6. Titanium | Glass Bead | 4.62 | 1.63 | 40 W | .36 |
| 6. Titanium | Glass Bead | 2.91 | 1.2 | 30 W | .41 |
| 7. Titanium | Satin | 4.62 | 4.85 | 40 W | 1.05 |
| 7. Titanium | Satin | 2.91 | 2.55 | 30 W | .88 |
| 8. Titanium | Blue Anodize | 4.62 | 1.3 | 40 W | .28 |
| 8. Titanium | Blue Anodize | 2.91 | .8 | 30 W | .27 |
| 9. Aluminum | Bright | 4.62 | .15 | 40 W | .032 |
| 9. Aluminum | Bright | 2.91 | .075 | 30 W | .026 |
| 10. Aluminum | Glass Bead | 4.62 | 1.25 | 40 W | .27 |
| 10. Aluminum | Glass Bead | 2.91 | .5 | 30 W | .17 |
| 11. Aluminum | Satin | 4.62 | 2.5 | 40 W | .54 |
| 11. Aluminum | Satin | 2.91 | 2.05 | 30 W | .70 |
| 12. Aluminum | Blue Anodize | 4.62 | 8.75 | 40 W | 1.90 |
| 12. Aluminum | Blue Anodize | 2.91 | 6.3 | 30 W | 2.16 |

Observations from Table III Tests

A visual inspection of the samples shown in Table III indicated that Sample 11 (aluminum with a satin finish) yielded much higher absorptivity without any sign of surface burnout. Some samples that showed higher levels of absorptivity also showed evidence of a damaged surface.

Samples 10 and 11 (aluminum with a glass bead finish and aluminum with a satin finish) were examined under a scanning electron microscope to study surface finish. The aluminum with the glass bead finish showed rounded impact craters as well as small pieces of glass embedded on its surface. The rounded craters are relatively good reflectors of light which explains the low absorptivity coefficient measured on this sample. Sample 11 with the satin finished aluminum shows a surface that smeared and is rougher locally providing more areas which trap the light. The rougher surface of the satin finish is believed to explain the higher absorptivity for the satin finished aluminum.

The conclusion that can be drawn from this test is that aluminum with a satin finish demonstrated an optimum condition, that is the highest coefficient of absorptivity without surface damage. Because of the promising results of aluminum with a satin finish on previous tests, it was decided to add a controlled thickness of anodized coating over a substrate of aluminum to give the effect of a composite material. The substrate of aluminum has a high thermal conductivity for diffusing or dissipating heat, and the aluminum oxide surface has a low free electron concentration and is, therefore, a good absorber of heat and light. Also, the melting temperature is above 2,000° C.

We decided to use 6061-T6 aluminum because it was highly corrosion resistant, readily available and had a very high thermal conductivity of 0.37 calorie/cm²/cm/degrees centigrade/second. We decided to vary the coating thickness from about 4 microns, which is about 40% of the wavelength of the carbon dioxide laser beam that was used. The surface coating was anodized aluminum oxide over a base of aluminum. Two sets of specimens were made, each with a different thickness of aluminum oxide coating. One set of specimens was exposed to a $CO_2$ laser with a ¼ to ½ millimeter spot size for one second exposures at a 40 watt power level. The other set of specimens was exposed to the same laser with the same spot size for the same time but at a 30 watt power level. The clear anodized aluminum coating varied in thickness from 4 to 12 microns. One specimen had no coating at all. The test results are shown in the following Table IV.

TABLE IV

| Coating Thickness | $\Delta T_1$ | $\Delta T_2$ | $A = \Delta T_2/\Delta T_1$ | Power |
|---|---|---|---|---|
| 4 M | 5.43 ± 3% | 5.0 | .92 | 30 W |
| 4 M | 7.0 ± 3% | 6.6 | .94 | 40 W |
| 6 M | 5.43 ± 3% | 5.25 | .97 | 30 W |
| 6 M | 7.0 ± 3% | 6.9 | .99 | 40 W |
| 8 M | 5.43 ± 3% | 5.4 | .99 | 30 W |
| 8 M | 7.0 ± 3% | 7.2 | 1.03 | 40 W |
| 10 M | 5.43 ± 3% | 5.5 | 1.01 | 30 W |
| 10 M | 7.0 ± 3% | 7.3 | 1.04 | 40 W |
| 12 M | 5.43 ± 3% | 5.5 | 1.01 | 30 W |
| 12 M | 7.0 ± 3% | 7.2 | 1.03 | 40 W |
| No Coating | 5.43 ± 3% | .5 | .09 | 30 W |
| No Coating | 7.0 ± 3% | .7 | .10 | 40 W |

Observations from Table IV Tests

All samples except for the uncoated samples show that they are very good absorbers. Only one or two of the samples hit by a 40 watt beam showed any kind of marking from the beam. There were whitish spots, but the area did not appear to be significantly damaged. It appears from the tests that anodized aluminum (6061-T6) makes a very effective absorber of laser energy. The coating thickness does not appear to be critical as long as it is at least 4 microns and not so thick as to prevent heat from being conducted from the coating to the underlying substrate so that it may be carried away to minimize the amount by which the temperature of the instrument will rise.

The glass bead surface on all test specimens was achieved by sandblasting the surface by well-known techniques.

The satin finish is achieved by buffing the surface with a cotton rag wheel having a 9" diameter spinning at 1400 to 1800 r.p.m. yielding a surface speed of 3300 to 4200 feet per minute. We applied heavy duty greaseless compound 240 grit (supplied by Roberts Rouge Company of Waterbury, Conn. called "Rouge Compound"). The cotton rag wheel was applied with light pressure to the surface of the specimen a maximum of three times to achieve the satin finish.

The black oxide surface is achieved by immersing a specimen in a boiling solution of "Black Magic SS" a granular material sold by Mitchell Bradford Chemical Company of Milford, Conn. and water using 4¾ pounds of "Black Magic SS" to make one gallon of solution at a temperature of 250° F. to 260° F. A specimen was left in the solution 2 to 15 minutes, usually 5 minutes, depending on how black a specimen was wanted, and then rinsed with cold water.

The clear anodized surface is achieved by the anodizing process set forth in Volume 2 of *Metals Handbook* (8th Edition, 1964, entitled "Heat Treating Cleaning and Finishing," page 620-626). We used the sulfuric acid anodizing process.

The present invention has been described in conjunction with certain preferred embodiments. Those skilled in the art will appreciate that many modifications and changes may be made to these preferred embodiments without departing from the scope of the present invention. It is, therefore, not intended to limit the present invention except as set forth in the attached claims.

We claim:

1. An instrument for intercepting a carbon dioxide incident laser beam after it has energized a desired surgical target site but before it energizes material adjacent to the surgical target site comprising:

a substrate means for transmitting energy received from a laser beam away from a surgical target site, said substrate means having a high thermal conductivity and an exterior surface;

a coating means for absorbing laser energy at the wavelength of a carbon dioxide laser, said coating means covering substantially the entirety of said exterior surface of said substrate means and having a high absorptivity for energy at the wavelength of said incident laser beam; and, said coating means having a thickness which is large enough to provide high absorptivity but small enough to permit absorbed energy to be readily transferred to said high conductivity substrate means, and said thickness of said coating means being not greater than 0.001 inch.

2. The instrument of claim 1 wherein said substrate means is aluminum and said coating means is aluminum oxide.

3. The instrument of claim 2 wherein said coating means is anodized aluminum oxide and the finish of said substrate means is a satin finish.

4. The instrument of claim 1 wherein said substrate means is copper and said coating means is stainless steel.

5. The instrument of claim 1 wherein said substrate means is copper and said coating means is a ceramic substance.

6. The instrument of claim 1 wherein said substrate means is aluminum and said coating means is a ceramic substance.

7. The instrument of claim 1 wherein said substrate means includes a thin strip having an axial dimension much greater than its transverse dimension and having at least one axially extending opening extending throughout its entire length to permit cooling fluid to be introduced therethrough.

8. The instrument of claim 7 wherein said substrate strip includes a plurality of channels extending axially completely along said strip from a single opening at the proximal end of said strip to a plurality of openings at the distal end of said strip; and further including a handle attached to said strip and adapted for providing fluid communication between a source of fluid and said channels.

9. The instrument of claim 7 wherein said axially extending opening along said strip has at least one branch extending from said opening in the transverse direction and at least one second axially extending opening in fluid communication with said branch and extending to the distal end of said strip.

10. The apparatus of claim 1 wherein said substrate means is an axially extending rod having an annular cross-section defining an axially extending opening wherein said opening in said annulus forms a channel through said rod to permit irrigation fluid to be introduced therethrough.

11. The apparatus of claim 10 further including a handle connected to said substrate means said handle having an opening therethrough for proving fluid communication between said channel and a source of fluid.

12. The instrument of claim 1 further including a base material of an existing surgical tool having an exterior surface, said substrate means affixed to at least a portion of said exterior surface.

13. The instrument of claim 1 wherein said substrate means is aluminum and said coating means is stainless steel.

14. An instrument for intercepting a carbon dioxide incident laser beam after it has energized a desired surgical target site but before it energizes material adjacent to the surgical target site comprising:

an aluminum substrate means for transmitting energy received from a laser beam away from a surgical target site, said substrate means having a high thermal conductivity and an exterior surface;

an aluminum oxide coating means for absorbing laser energy at the wavelength of said incident laser beam, said coating means covering substantially the entirety of said exterior surface of said substrate means and having a high absorptivity for energy at the wavelength of said incident laser beam and;

said coating means having a thickness which is large enough to provide high absorptivity but small enough to permit absorbed energy to be readily transferred to said high conductivity substrate means, and said coating means thickness being substantially in the range of 4 microns to 12 microns.

* * * * *

UNITED STATES PATENT AND TRADEMARK OFFICE

Certificate

Patent No. 4,580,558                  Patented April 8, 1986

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Rene J. Cabrera, Thomas W. Eagar, and John A. Santangelo.

Signed and Sealed this fourth Day of November, 1986.

BRADLEY R. GARRIS,
*Office of the Deputy Assistant
Commissioner for Patents.*